(12) United States Patent
Johnson

(10) Patent No.: US 10,058,463 B2
(45) Date of Patent: Aug. 28, 2018

(54) MALE UNDERGARMENT FOR HOLDING ABSORBENT PAD

(71) Applicant: EZ Male Pads, Inc., Long Beach, CA (US)

(72) Inventor: Wade C. Johnson, Long Beach, CA (US)

(*) Notice: Subject to any disclaimer, the term of this patent is extended or adjusted under 35 U.S.C. 154(b) by 333 days.

(21) Appl. No.: 14/940,068

(22) Filed: Nov. 12, 2015

(65) Prior Publication Data

US 2017/0135875 A1    May 18, 2017

(51) Int. Cl.
*A41B 9/02* (2006.01)
*A61F 13/70* (2006.01)
*A61F 13/62* (2006.01)
*A61F 13/66* (2006.01)

(52) U.S. Cl.
CPC .............. *A61F 13/70* (2013.01); *A41B 9/02* (2013.01); *A61F 13/622* (2013.01); *A61F 13/665* (2013.01)

(58) Field of Classification Search
CPC ........... A41B 9/02; A61F 13/70; A61F 13/622
USPC ...................................................... 2/400–405
See application file for complete search history.

(56) References Cited

U.S. PATENT DOCUMENTS

| | | | | |
|---|---|---|---|---|
| 2,486,499 A * | 11/1949 | Schoendorf | ............... | A41B 9/02 2/404 |
| 2,872,685 A * | 2/1959 | Denbo | .................... | A41B 9/02 2/403 |
| 4,326,302 A | 4/1982 | Lowe et al. | | |
| 5,070,869 A * | 12/1991 | Zhang | ....................... | A41B 9/02 2/403 |
| 8,087,098 B2 * | 1/2012 | Kimberly | ............... | A41B 9/001 2/227 |
| 8,555,422 B2 * | 10/2013 | Steele | .................... | A41B 9/023 2/400 |
| 2013/0174328 A1 * | 7/2013 | Rolon | .................... | A41B 9/023 2/403 |

FOREIGN PATENT DOCUMENTS

JP    1104382 C    7/1982
JP    2013209755 A    10/2013

OTHER PUBLICATIONS

International Search Report dated Aug. 11, 2016 issued by Korean Intellectual Property Office for PCT/US2015/065595.

* cited by examiner

*Primary Examiner* — Katherine Moran
(74) *Attorney, Agent, or Firm* — Fulwider Patton LLP

(57) ABSTRACT

A male undergarment that holds an absorbent pad has a waistband and first and second pant portions and a centered hole. A trapezoidal flap is placed over a front panel where the first and second sides of the trapezoidal flap are sewn into the garment, such that the sewn portion of the trapezoidal flap covers the hole. The unattached first and second sides of the trapezoidal flap are releasably secured to the garment via complimentary snaps and snap holders, such that when the snaps are engaged to the snap holders a pouch is formed by the trapezoidal flap and the garment.

4 Claims, 4 Drawing Sheets

US 10,058,463 B2

MALE UNDERGARMENT FOR HOLDING ABSORBENT PAD

BACKGROUND

The present invention relates generally to adult incontinence, and more particularly to an undergarment for holding a urine absorbent pad that protects the wearer from moisture and is easily accessible in the upright or prone position.

Urinary incontinence (UI) is defined as the involuntary loss of urine. In both men and women, age is a consistently reported risk factor for UI; however, it is not considered a normal consequence of aging. Overall, UI affects up to 30% of community dwelling older adults and more than 50% of nursing home residents. Despite its high prevalence, up to one-half of cases may not be reported because individuals with UI may not seek medical intervention. Embarrassment and the perception that UI is an expected consequence of aging are common factors in the failure to seek a solution or treatment. That reluctance is particularly strong in men, who often deem the problem to be associated with a loss of masculinity.

Urinary incontinence is categorized according to pathophysiology and clinical presentation. The four main categories are (1) stress urinary incontinence (SUI), (2) urge urinary incontinence (UUI), (3) overflow incontinence, and (4) functional incontinence. Mixed types of incontinence are common and may complicate diagnosis and treatment because of overlapping symptoms. Studies have found that UI significantly affects psychological well-being and health care-related quality of life. Urinary incontinence may impair sexual function, restrict activities, interfere with interpersonal relationships, decrease self-esteem, increase caregiver burden, increase financial burden, and cause anxiety or depression. It is a common precipitant of institutionalization in older adults.

Because of current demographic trends, UI is an increasingly common medical and socioeconomic problem. One place where the issue arises with great propensity is nursing homes, where older patients often suffer moderate to severe UI due to a variety of physiological conditions. In men, incontinence is often related to prostate problems or treatments that become exacerbated in the elderly. Certain medical conditions, particularly those affecting the brain or nervous system, such as Alzheimer's, Parkinson's, Dementia, Multiple Sclerosis and brain damage, can also lead to incontinence. This is due to the nerve passageways from the brain becoming damaged. The result can be either an overactive bladder (the need to go often and frequently) or an under-active bladder (ineffective emptying leading to leakage). Diabetes and or a stroke can also bring on incontinence.

With aging, bladder capacity decreases, ability to inhibit urination declines, involuntary bladder contractions (detrusor overactivity) occur more often, and bladder contractility is impaired. Thus, voiding becomes more difficult to postpone and tends to be incomplete. Postvoid residual volume increases in as much as ≤100 mL (normal<50 mL). A weakening of the endopelvic fascia often results as well. In men, the tendency for the prostate to enlarge with age causes the partial obstruction of the urethra, leading to incomplete bladder emptying and strain on the detrusor muscle. These changes occur in many normal, continent elderly males and may facilitate incontinence but do not cause it.

One challenge associated with male incontinence is the necessity for changing clothing, bedding, and other items that may become soiled due to an incontinence patient. When a disabled patient has voided his urine, the caregiver must remove the patient's clothing and bedding while the patient is in a prone position. This can be challenging to the caregiver, who must lift the patient to remove the clothing and bedding while simultaneously trying to extract the soiled garments and sheets, blankets, etc. If the patient is large or overweight, the problem becomes magnified even greater.

Elderly patients and residents of nursing homes who are immobile or have reduced mobility are at high risk for developing pressure ulcers (bed sores). This condition is made worse if the patient is incontinent because the moisture from urine causes the surface of the skin to become irritated and infected. For this reason, it is important to prevent urine from remaining in contact with the skin for any extended period of time, and that it be removed as soon as possible.

The U.S. Census Bureau estimates there are 76.4 million baby boomers, and the oldest of this generation, which includes those born between 1946 and 1964, are over 65 years old. For many of these people, adult diapers are a way to ameliorate the effects of moderate to severe incontinence. Adult diapers are a $7 billion global market, and sales have grown more than 8 percent over the past five years due to this increasing number of baby boomers entering their 70s and 80s. This trend appears to be rising as the stigma of wearing protective undergarments becomes less and the popularity of these products grow.

However, for males, particularly invalid males, diapers can be an unsatisfactory solution for several reasons. First, the previously raised issue that, once soiled, the patient must be changed like an infant by a caregiver who may not have the strength to lift a full grown adult male. Changing a diaper can lead to the patient being moved in positions that may strain or injure the patient, particularly when moved by a caregiver with inadequate strength to properly maneuver a full grown adult male. Second, unlike females where the origin and direction of the urine stream is fairly predictable, males tend to urinate from different positions, angles, and directions, and this inconsistency leads to leakage. This is especially true when the patient is lying on his back and suffers incontinence, because a gap in the top of the diaper at the patient's stomach can provide an opening where urine can leak outside of the diaper, leading to the issues raised above. Patients who go frequently can get ignored because of the challenges in changing the patient, leading to health issues as well.

One solution attempted to address male incontinence is found in U.S. patent application Ser. No. 14/673,549 entitled "Urine Absorbent Pad", assigned to the present assignee and fully incorporated by reference herein in its entirety. The pad is a multi-fold pad worn by a male user to prevent moisture from escaping against the wearer's skin, whether prone or upright. The present invention is designed to be used in conjunction with the pad of the '549 application to provide an easy to wear undergarment that holds the pad and allows the pad to be quickly replaced when necessary.

SUMMARY OF THE INVENTION

The present invention is a male undergarment having a waistband and first and second pant portions terminating at leg holes. Approximately centered on the undergarment is a hole sized to allow a male genitalia to pass through so that the garment fits snugly against the wearer's torso and legs. A seam runs from a first leg hole to a second leg hole, and a trapezoidal flap is attached to the seam. A portion of the first and second sides of the trapezoidal flap are sewn into the respective first and second pant portions, such that the sewn portion of the trapezoidal flap covers the hole while approximately half of the first and second sides of the trapezoidal flap remain unattached to the garment. The unattached first and second sides of the trapezoidal flap are releasably secured to the garment via complimentary snaps and snap holders, such that when the snaps are engaged to the snap holders a pouch is formed by the trapezoidal flap and the garment. It should be noted that the releasable attachment can also be made by buttons, hooks, hook and loop fasteners, etc. In a preferred embodiment, a snap is located top center of the flap to engage a snap holder placed at the waistband of the garment to "close" the pouch. Thus, the garment forms a semi-openable pouch that can be fully closed to capture a urine absorbent pad and allows for quick exchange of the pads by releasing the flap and replacing the old pad with the new.

These and other features of the invention will best be understood in light of the detailed description of the invention in conjunction with the accompanying drawings listed below.

DETAILED DESCRIPTION OF THE PREFERRED EMBODIMENTS

Figure 1:
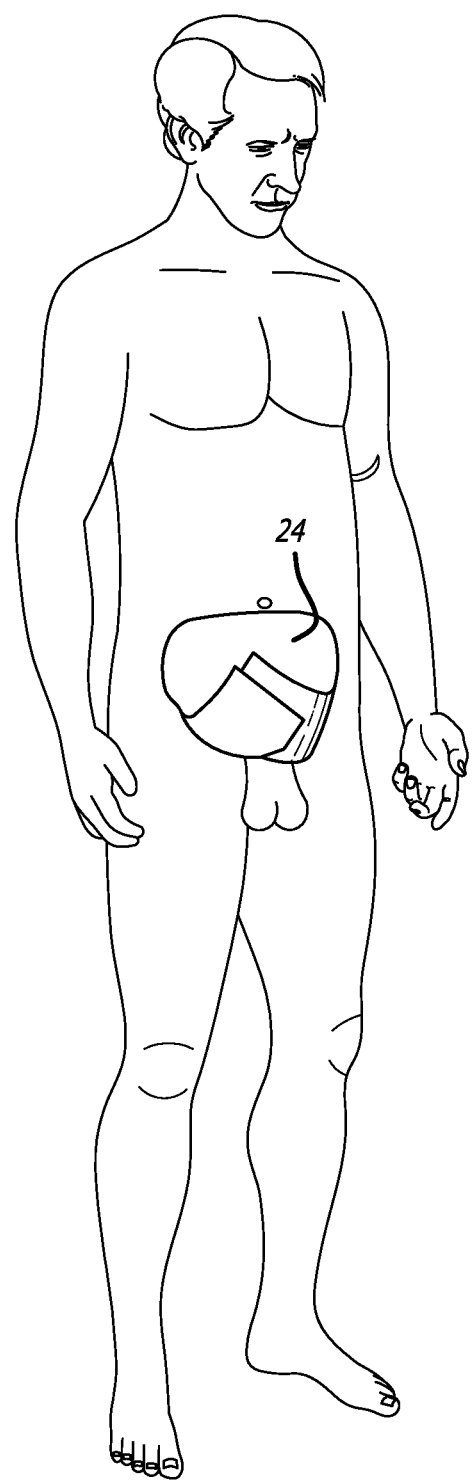
FIG. 1 is a perspective view of a pad that may be used with the present invention.

Absorbent pads used to assist those with incontinence are well known in the art. U.S. patent application Ser. No. 14/673,549 describes one such pad, depicted generally in FIG. 1. The pad 24 has a number of folds and creases that allow a male wearer to avoid urine from reaching the skin where it can create other health and safety concerns. The present invention is designed to carry the pad shown in FIG. 1 in a convenient and reliable manner that works for ambulatory and non-ambulatory wearers alike.

Figure 2:
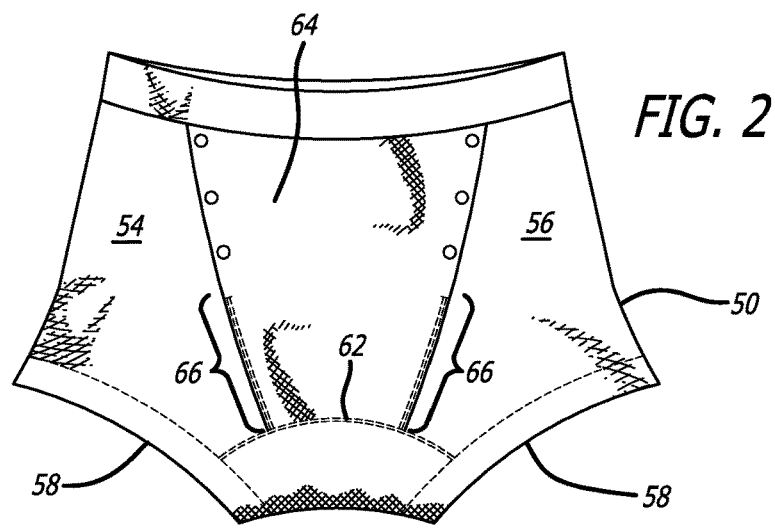
FIG. 2 is an enlarged perspective view of the garment of the present invention.
Figure 3:
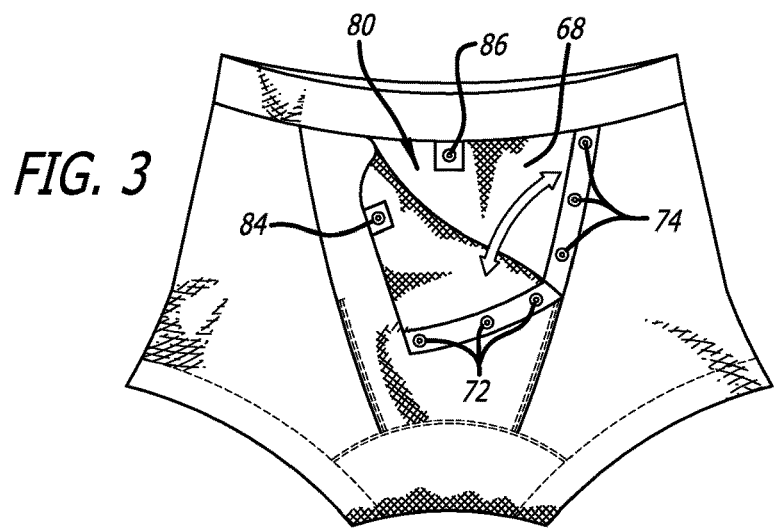
FIG. 3 is a perspective view of the garment with the flap partially folded down.
Figure 4:
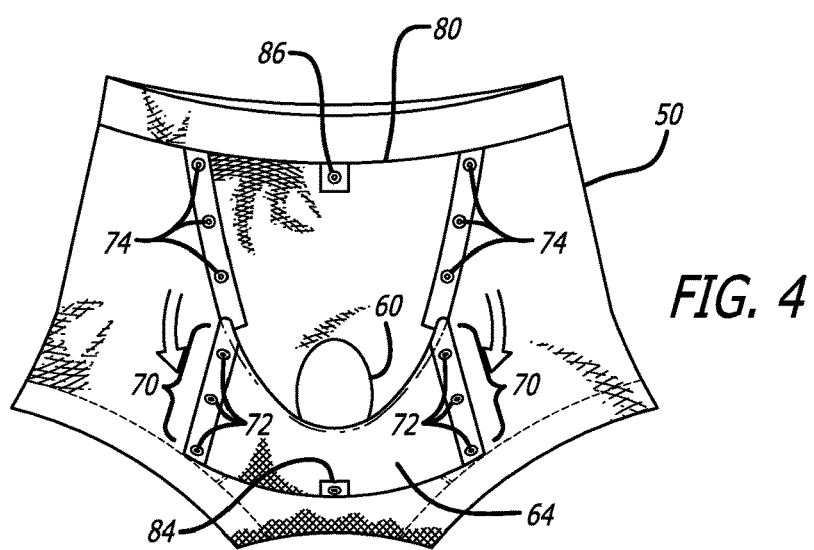
FIG. 4 is a perspective view of the garment with the flap fully folded down.

FIG. 2 illustrates an undergarment 50 that is designed to hold the pad 24 in a specially designed pouch. The undergarment 50 has a waistband 52 and first and second pant portions 54,56 terminating at leg holes 58. Approximately centered on the undergarment is a hole 60 (see FIG. 3) sized to allow a male genitalia to pass through so that the garment 50 fits snugly against the wearer's torso and legs. A seam 62 runs from a first leg hole to a second leg hole, and a trapezoidal flap 64 is attached to the seam 62 at the bottom edge of the flap. In a preferred embodiment, a portion of the first and second sides 66 of the trapezoidal flap 64 is sewn into the respective first and second pant portions 54,56, such that the sewn portion 66 of the trapezoidal flap 64 covers the hole 60 while approximately half of the first and second sides of the trapezoidal flap 64 remain unattached to the garment 50 (see FIG. 4). The unattached first and second sides 70 of the trapezoidal flap 64 may be releasably secured to the garment 50 via complimentary snaps 72 and snap holders 74, such that when the snaps 72 are engaged to the snap holders 74 a pouch 80 is formed by the trapezoidal flap 64 and the garment 50. The pouch 80 is formed on the outer portion of the undergarment 50 between the front panel 68 of the garment and the trapezoidal flap 64, and is partially releasable, in that part of the pouch 80 is sewn into the garment and part of the pouch can be separated from the garment by releasable attachment mechanisms such as snaps, Velcro® type hook and loop fastener material, buttons, and the like (hereafter "snaps" for convenience). The flap 64 folds down over the front panel 68 at the mid-sides where the sewn portion 66 of the flap 64 terminates, and then when the snaps 72 are engaged the flap 64 is attached along three sides of the garment and the pouch 80 is fully established. A closure snap 84 centered on the top side of the flap 64 adjacent the waistband 52 cooperates with the snap holder 86 to allow the pouch 80 to be closed from the top to prevent the pad 24 from coming out of the pouch 80 during sleep or through normal motion of the body.

Figure 5:
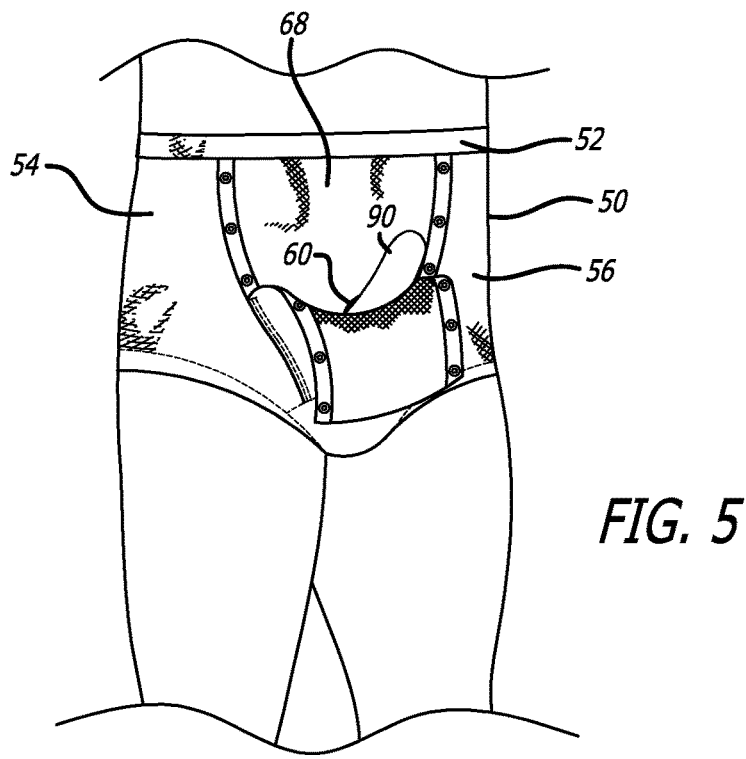
FIG. 5 is a perspective view of the garment on a user with the flap folded down.
Figure 6:
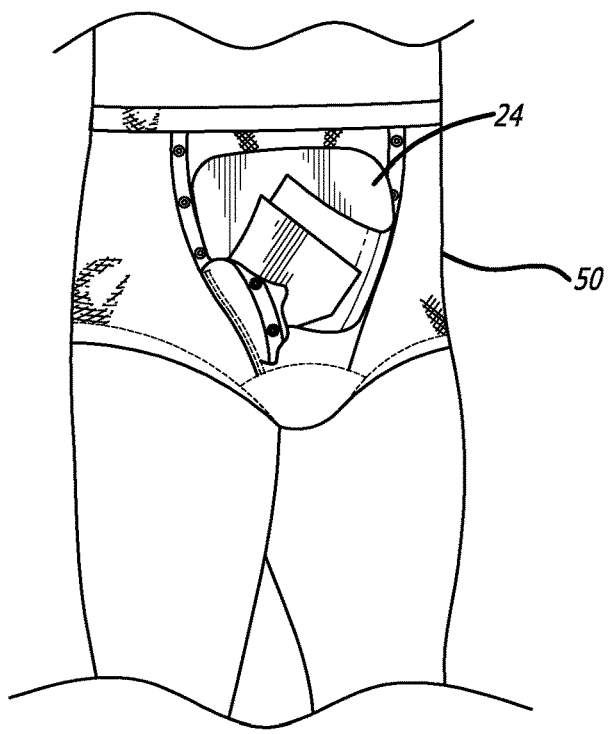
FIG. 6 is a perspective view of the garment with the flap removed and the pad in place.
Figure 7:
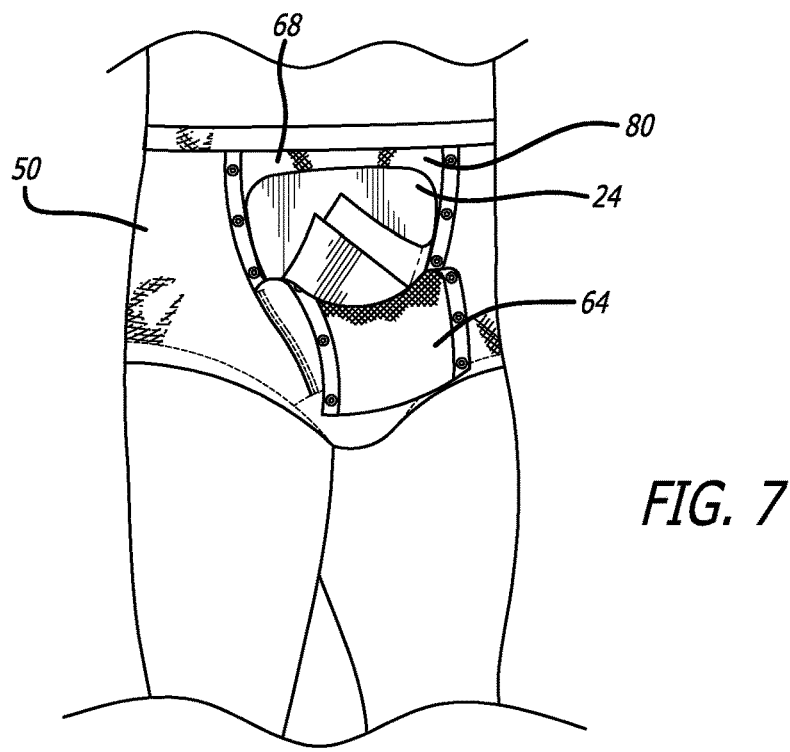
FIG. 7 is a perspective view of the garment with the flap open and the pad in place.
Figure 8:
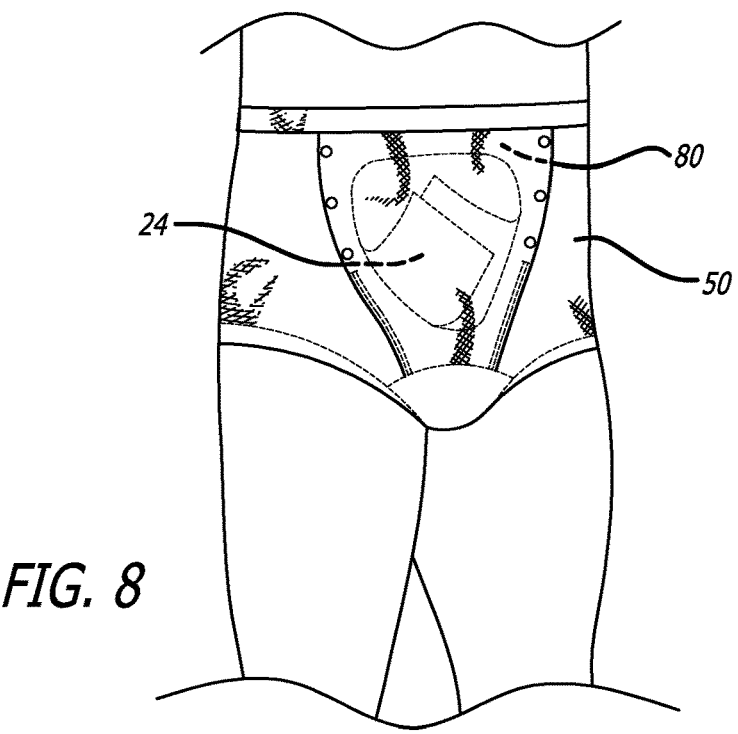
FIG. 8 is a perspective view of the garment with the flap closed, enclosing the pad.

FIG. 5 illustrates the garment 50 on a wearer, where the flap has been folded down for clarity. The hole 60 is centered on the front panel 68, below the waistband 52 and between the first and second pant portions 54,56, and sized to pass the wearer's genitalia 90 through. FIG. 5 illustrates the garment 50 with the wearer's genitalia through the hole. FIG. 6 illustrates the garment with the pad in place about the wearer's genitalia (still with the flap removed for clarity), and FIG. 6 illustrates the garment with the pad 24 in place and the flap removed to show the details. As can be seen in FIG. 7, the access of the pad 24 in the pouch 80 is enhanced by the capability of the flap 64 to partially fold over the front panel 68 once the snaps 72 are disengaged from the snap holders 74. This allows easy removal and replacement of the pads and allows the pads to be applied to the user with the garment 50 on. FIG. 8 shows the garment 50 on the wearer with the pad 24 (shown in shadow) in place, the snaps engaged to close the pouch 80 and fully secure the pad therein.

The present invention provides an expedient and comfortable garment that is designed to be used with absorbent pads to assist those with incontinence, and is well suited for user's who are ambulatory as well as non-ambulatory. The ease with which pads can be replaced using the present invention allows those who suffer from incontinence to carry a second pad in a pants pocket, and when the need arises simply excuse one's self to use the restroom. Once there, the trapezoidal flap can be quickly opened by releasing the snaps, the used pad removed and discarded, and the new pad applied easily. The pouch is then re-closed and the wearer can return to whatever activity he was engaged with prior. The pads and the design of the garment keep the garment itself dry and also prevent the wearer's skin from prolonged contact with any urine due to the absorbent material in the pad, so there is no leakage and no prolonged exposure of the wearer to the body fluid. The solution of the present invention greatly enhances a quality of life for those afflicted with moderate to severe incontinence.

The present invention has been described with respect to a preferred embodiment of the present invention using the inventor's best mode of carrying out the invention. One of ordinary skill in the art would readily recognize many modifications and substitutions that could be applied to the present invention without departing from the spirit of the present invention, and the scope of the invention should include all such modifications and substitutions. Accordingly, the scope of the present invention should not be limited by any specific drawing or characterization in the detailed description of the invention, but rather by the words of the appended claims using the plain and ordinary meanings of those words in light of the descriptions herein.

I claim:

1. A male undergarment, comprising a waistband and first and second pant portions terminating at leg holes and connected by a lower seam, and a front panel defined between the first and second pant portions and between the waistband and the lower seam, the front panel including a circular hole;

a trapezoidal flap having a lower edge, first and second equal side edges, and an upper edge longer than the lower edge, the trapezoidal flap attached to the seam at the lower edge and a lowermost portion of the first and second side edges are sewn into the front panel such that the sewn portion of the trapezoidal flap covers the hole;

releasable fasteners attached to unattached portions of the first and second side edges of the trapezoidal flap for engagement with mating releasable fasteners on the front panel, such that when the releasable fasteners on the first and second side edges of the trapezoidal flap are connected to the mating releasable fasteners on the front panel, then a pouch is formed by the trapezoidal flap and the front panel.

2. The male garment of claim 1, wherein a releasable closure means is additionally placed on the longer upper edge of the trapezoidal flap for engagement with a mating releasable fastener on the front panel at the waistband to provide a closure for the pouch along an upper edge.

3. The male garment of claim 2, wherein the releasable fasteners are snaps.

4. The male garment of claim 2, wherein the releasable fasteners are hook and loop fastening material.

\* \* \* \* \*